United States Patent [19]

Taylor

[11] Patent Number: 4,553,969

[45] Date of Patent: Nov. 19, 1985

[54] DISPOSABLE RELIEF CONTAINER WITH SECURAL LINER

[76] Inventor: Frances H. Taylor, 218-B South St., Eatontown, N.J. 07724

[21] Appl. No.: 475,220

[22] Filed: Mar. 14, 1983

[51] Int. Cl.$^4$ .............................................. A61F 5/44
[52] U.S. Cl. ................................................. 604/355
[58] Field of Search ............... 604/355, 356, 342–346, 604/277, 348; 383/109, 113, 93, 95, 11, 103; 4/144.3, 661

[56] References Cited

U.S. PATENT DOCUMENTS

| | | | |
|---|---|---|---|
| 2,277,043 | 3/1942 | Cohn | 604/348 |
| 3,089,493 | 5/1963 | Galindo | 604/342 |
| 3,103,930 | 9/1963 | Collett et al. | 604/355 |
| 3,385,298 | 5/1968 | Fenton | 604/339 |
| 3,421,506 | 1/1969 | Priebe | 604/344 |
| 3,577,989 | 5/1971 | Anderson | 604/348 |
| 4,387,712 | 6/1983 | Briggs et al. | 604/333 |

FOREIGN PATENT DOCUMENTS 7703562  10/1978  Netherlands ..................... 604/318

Primary Examiner—C. Fred Rosenbaum
Assistant Examiner—J. L. Kruter
Attorney, Agent, or Firm—Louis E. Marn

[57] ABSTRACT

A disposal relief container for the collection and disposal of fecal material from the natural excremental passage ways of the human body comprising a gas permeable, flexible, fluid tight outer container, a flexible fluid tight inner container disposed within the outer container, the inner container having an opening coincidental with the opening of the outer container, a planer, pliable annular surface about the opening of the outer container, such annular surface having an adhesive means attached thereto to secure the disposal relief container to the human body, a plurality of air vents disposed on the inner container to permit the gaseous communication from the inner container to the atmosphere through the air vents and the gas permeable outer container and an adhesive means for securing the relief container in a closed condition after use for disposal or storage.

5 Claims, 6 Drawing Figures

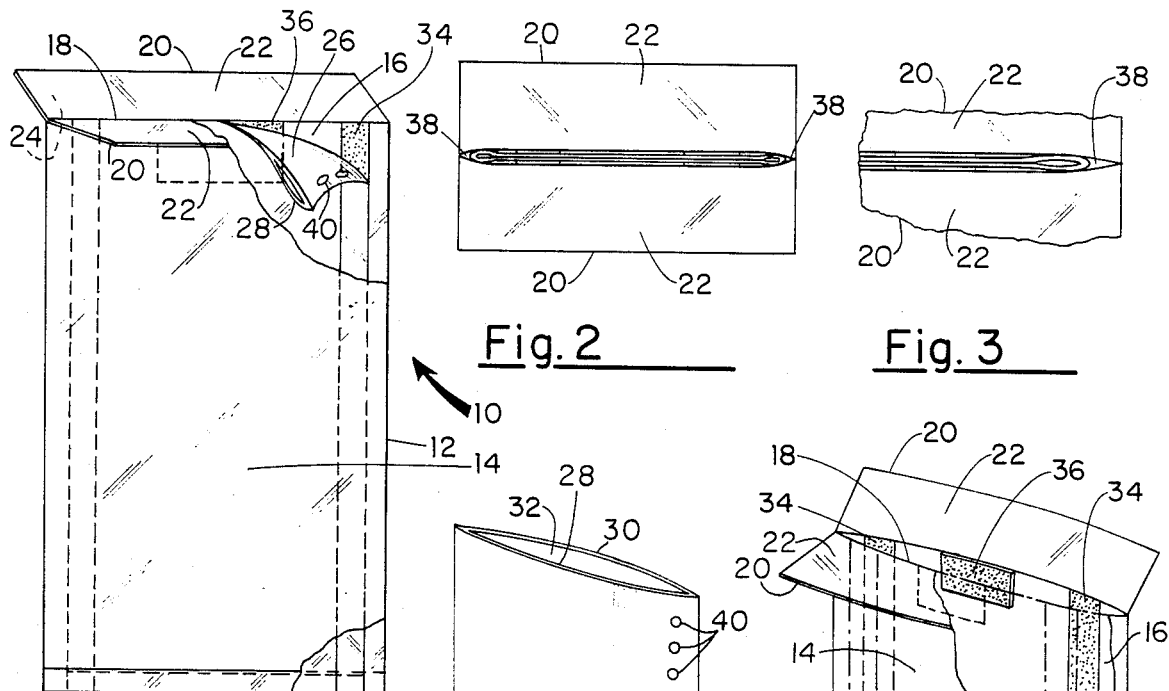
Fig. 1
Fig. 2
Fig. 3
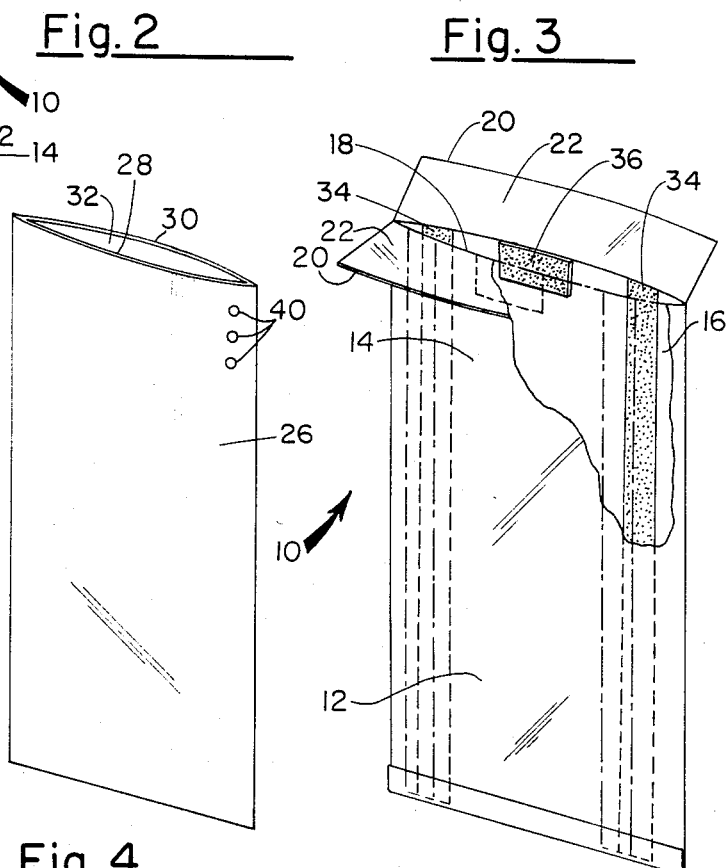
Fig. 4
Fig. 5
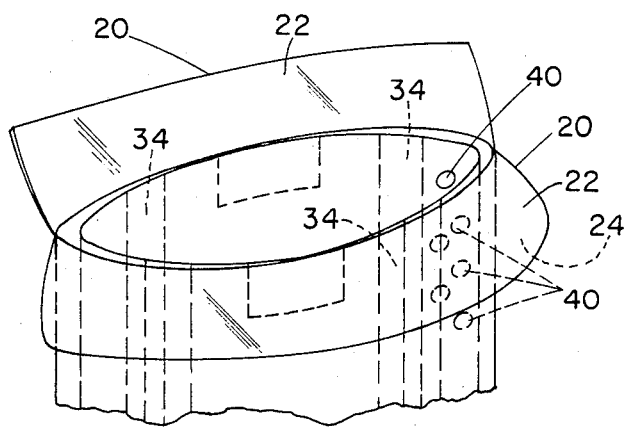
Fig. 6

DISPOSABLE RELIEF CONTAINER WITH SECURAL LINER

FIELD OF THE INVENTION

The invention relates to a disposable relief container, and more particularly to a disposable relief container for incontinent patients or the like or for use by individuals in an enclosed or confined environment.

BACKGROUND OF THE INVENTION

Individuals who are in good health, but who must remain in confined quarters or environments for relatively long periods of time without the opportunity to utilize standard toilets and the like, such as astronauts, have need for a relief container which can be used sanitarily and effectively and which is relatively light, and readily disposable or adaptable for storage. Reference is hereby made to U.S. Pat. No. 3,421,506 to Webb wherein there is disclosed a relief container developed pursuant to a National Aeronautics and Space Administration contract. The relief container is designed for use by astronauts placed in a relatively confined area for long periods of time. The device disclosed therein is a fecal collection device comprising a waterproof plastic bag 11 having a radial flange 13 on which there is positioned an adhesive 14 securing the relief container to the individual. This particular relief container also contains a finger stall 20 in a form of a plastic sleeve for aid in positioning the relief container. The relief container is sealable after use such that it can be stored or discarded.

In addition to the foregoing, individuals who are ill, bedridden or are incontinent usually require some aid in performing excremental body functions. This aid may take the form of a bed pan or a device which is inserted within the elimination tract to divert the excremental material into a tube connected to a container in a somewhat unnatural fashion such as a catheter or any ileostomy appliance. A third method of aid is the use of a device which is disposable and which is easily secured about the anus for the collection of excremental bodily functions. This type of device is identified as a so called natural form of elimination-trapping device. These devices are designed to be removably secured to the individual and do not interfere with or create a diversion of the individuals elimination tract. These devices have not been without problems for they usually require the patient to assume an uncomfortable position in order to render the device operative and often times the absence of a secure seal around the elimination tract duct and the recepticle or the presence of a defective seal create additional problems with respect to leakage. Additionally, none of the present devices in use address the problem associated with that of gas generated during the excremental function with the resultant possibility of a ruptured seal or a ruptured container.

With reference to relief containers for ill, bedridden or incontinent patients, attention is directed to U.S. Pat. No. 3,577,989 to Anderson which discloses a disposable plastic elimination trapping bag for incontinent patients which bag is designed for collection of not only Fecal matter, but also urine. U.S. Patent 3,577,989 is designed for utilization with the natural excremental passage ways of the human body but does not disclose the elements of the present invention. U.S. Pat. No. 3,089,493 to Galindo, U.S. Pat. No. 3,373,745 to Benfield, U.S. Pat. No. 2,639,710 to Fazio and U.S. Pat. No. 3,439,679, to Doolittle are exemplary of a colostomy or ileostomy devices which are not secured to the anus. These references are cited as of interest since the present invention does not relate to colostomy or ileostomy bags, but rather, to a relief container which utilizes the natural excremental passage ways of the human body.

OBJECTS OF THE INVENTION

An object of the present invention is to provide a novel disposable relief container for use by an individual during the natural elimination process of the individual.

A further object of the invention is to provide a novel disposable relief container which is shaped for the most effective attachment to the individual and which is easily positioned by the individual.

A still further object of the present invention is to provide a novel disposable relief container which provides a fluid tight seal between the container and the individual and which container provides for the collection of excrement but permits the escape of gases so as not to destroy the fluid tight seal between the container and the individual nor damage the container.

SUMMARY OF THE INVENTION

These and other objects of the present invention are achieved by a disposable relief container comprising a flexible, fluid tight, double lined container having an inner and outer container, each having a coincidental open end, the outer container having adhesive flange members for attachment of the container to the body of the individual, a plurality of air vents disposed on the inner bag proximate to the open end and the flange members of the outer container and an adhesive means for securing the relief container in a closed, secure condition for disposal or storage after use.

BRIEF DESCRIPTION OF THE DRAWINGS

A better understanding of the present invention as well as other objects and advantages thereof will become apparent upon consideration of the detailed disclosure thereof especially when taken with the accompanying drawings wherein FIG. 1 is a front elevational view containing a partial cut-away of the disposable relief container.

FIG. 2 is a top planer view of the disposable relief container.

FIG. 3 is a top planer enlarged cut-away view of the disposable relief container.

FIG. 4 is a perspective view of the plastic inner liner of the relief container.

FIG. 5 is a perspective front elevational view of the disposable relief container with a partial cut-away of the fastening means.

FIG. 6 is a perspective view of the upper portion of the disposable relief container.

DETAILED DESCRIPTIONS OF THE DRAWINGS

Referring now to FIG. 1 there is shown a front elevational, partial cut-away view of a disposable relief container of the present invention generally designed as 10. Disposable relief container 10 comprises an outer container member 12 having a generally rectangular configuration and comprised of a first side member 14 and a second side member 16 secured along their common longitudinal edges and one lateral edge so as to define said outer container member 12, having an opening 18 along one lateral edge. Outer container member 12 is formed or secured thereto about opening 18, with flange members 20 which extend about the opening 18. Flange members 20 comprise an upper surface 22 and a lower surface 24. Upper surface 22 of the flange member 20 is coated with a bacteria free adhesive which is utilized to secure disposable relief container 10 to the natural excremental passageway of an individual as will be more fully hereinafter discussed.

Relief container 10 includes, an inner container member 26. Inner container member 26 referring particularly to FIG. 4 is of a rectangular configuration having a first side member 28 and a second side member 30. Side members 28 and 30 are secured along their common longitudinal edges and one lateral edge so as to define inner container member 26 having an opening 32 at one lateral edge of inner container member 26.

Inner container member 26 is disposed within outer container member 12 and secured within outer container member 12 by means of longitudinally extending adhesive strips 34 and lateral adhesive strips 36 disposed on the inner surface of side members 14 and 16 of outer container member 12. Inner container member 26 thus disposed within outer container member 12 forms a double lined container member with openings 18 and 30 coinciding for the receipt of excrement.

Referring to FIGS. 2 and 3 there is shown a planer view and an enlarged planer view respectively of disposable relief container 10 with flange member 20 extending outwardly in a horizontal configuration. FIG. 3 provides a cutaway, blow up view of FIG. 2 serving to detail the positioning of inner container member 26 within outer container member 12. As can be readily seen in detail in FIG. 3, inner container member 26 is compressed such that sidewall members 28 and 30 are in intimate contact with each other and outer container member 12 is in a compressed state such that the inner surface of sidewall members of 14 and 16 are in intimate contact with the outer surface of sidewall members of 30 and 28 of inner container member 26. Inner container member 26 is positioned within outer container 12 by longitudinal adhesive strips 34 and lateral adhesive members 36 on the inner surfaces of side 14 and 16 of outer container member 12. In this configuration, it can be seen that there is an elongated channel 38 between each of the common longitudinal edges of inner container member 26 and the common longitudinal edges of outer container member 12. These longitudinal channels 38 extend longitudinally on both longitudinal edges of inner container member 26.

Along one longitudinal edge of inner container member 26, proximate to lateral opening 32 of said inner container member 26, there is formed a plurality of openings 40. Openings 40 are positioned along one longitudinal edge of inner container member 26 and are of such size as to permit the communication of gas from the interior of inner container member 26 into longitudinal channels 38.

Referring now to FIGS. 4, 5 and 6 there is shown prospective cutaway views of disposable relief container 10 depicting the relationship between inner container member 26 and outer container member 12 in the open position. It can be seen by reference to FIG. 6 that when a disposable relief container 10 is opened such that opening 18 of outer container member 12 and opening 32 of inner container member 26 form an open or eliptical opening, the longitudinal channels 38 between inner container member 26 and outer container member 12 still remain thus permitting the gaseous communication between inner container member 26, and elongated channels 38 by means of a plurality of openings 40 in inner container member 26.

In the preferred embodiment of a disposable relief container 10, inner container member 26 is constructed of a impermeable, pliable yet resilient plastic and outer container member 12 is constructed of a gas permeable, fluid impermeable, pliable yet resilient paper with adhesive coated on the upper surface 22 of flange member 20. The adhesive disposed on upper surface 22 of the flange member 20, may be protected by a removable paper layer prior to the individuals use of the disposable relief container 10.

In use, the removable protective layer of paper would be removed from the adhesive coating on the upper surface 22 of the flange member 20 and disposable relief container 10 would be opened and positioned such that coincidental openings 18 and 32 of outer container member 12 of inner container member 26 respectively would coincide with the individual's anus. Flange members 20 being of a pliable yet resilient material are designed to overlie and be tightly sealed against the curved body portion of the patient in the vicinity of the anus providing a fluid tight sealing engagement with the body around the anus.

In this configuration, outer container member 12 and inner container member 26 are positioned to receive the eliminated material from the patient. Openings 40, in inner container member 26 permit the escape of gas during the elimination process so as to insure the integrity of the seal between flange members 20 and the body portion of a patient. Additionally, openings 40 in inner container member 26 permit the passage of gas from inner container member 26 into elongated channels 38 and thence to the atmosphere through gas permeable outer container member 12, so as to insure the integrity of disposable relief container and prevent the rupture and subsequent leakage of same due to increased pressure from the build up of gas within disposable relief container 10 and to also prevent the possible rupture of the seal between flange member 20 and the patients body.

When the excremental function is completed, disposable relief container 10 is easily removed from the patients body by peeling flange members at 20 from the body portion of the patient. Disposable relief container 10 is then easily and quickly sealed for disposal by folding flange member 20 such that the adhesive layers on upper surfaces 22 are folded upon each other effectuating a seal of the contents of disposable relief container 10. In this configuration, disposable relief container 10 may be discarded or in the case of use by a healthy individual in a confined or closed environment, disposable relief container 10 may be stored until time for suitable disposable.

Disposable relief container 10 is easily and quickly attached and detached from the patient without requiring excessive or uncomfortable movement of the patient and is positioned when attached to the patient so as to not interfere with the patients movement. In use, the plurality of openings 40 in disposable relief container 10 insures that the antibacterial seal of flange members 20 with the patients body portions, will not be broken by the release of gas into disposable container 10 but rather, said gas will be provided with a means of exiting disposable container 10 without effecting the fluid tight integrity of disposable relief container 10 as it relates it to excreted material gathered from the patient. Thus, the openings 40 in inner container member 26 insure the integrity of the seal of flange members 20 with the patients body portions and insures the integrity of the double lined disposable relif container 10 from rupture.

While the invention has been described in connection with the exemplary and embodies thereof, it will be understood that there will be many modifications apparent to those of ordinary skill in the art and that this application is intended to cover any adaptations or variations thereof. Therefore, it is manifestly intended that this invention be only limited by the claims and the equivilents thereof.

I claim

1. A disposable relief container for the collection and disposal of fecal material from the natural excremental passageway of a human body, which comprises:
    a gas permeable, fluid impermeable, flexible outer container having an opening and formed with flange members having a bacteria-free adhesive coated thereon for attachment to said human body about said natural excremental passageway; and
    a flexible, fluid tight inner container having an opening, said inner container positioned in and mounted to said outer container by means of longitudinal and lateral adhesive strips secured to an interior surface of said outer container whereby said opening of said inner container is coincidental with said opening of said outer container, said inner container provided with vent means for gaseous communication to the atmosphere via said inner and outer containers.

2. A disposable relief container for the collection and disposal of fecal matter as defined in claim 1 wherein said inner container disposed within said outer container is such that a longitudinal channel is formed between longitudinal edges of said inner container with said outer container.

3. A disposable relief container for the collection and disposal of fecal material as defined in claim 1 wherein said means for gaseous communication from said inner container to atmosphere comprises a plurality of air vents formed in said inner container proximate to said opening, said air vents cooperating with said gas permeable, flexible, fluid tight outer container to permit the passage of gas from said inner container through said air vents and through said gas permeable outer container to said atmosphere.

4. A disposable relief container for the collection of disposable fecal material as defined in claim 1 wherein said adhesive is provided with a removable protective coating.

5. A disposable relief container for the collection and disposal of fecal material as defined in claim 1 and further including means for securing said relief container in a closed condition for disposal and storage and comprises said adhesive.

* * * * *

UNITED STATES PATENT AND TRADEMARK OFFICE
CERTIFICATE OF CORRECTION

PATENT NO. : 4,553,969
DATED : November 19, 1985
INVENTOR(S) : Frances H. Taylor It is certified that error appears in the above-identified patent and that said Letters Patent is hereby corrected as shown below:

In the Title

Delete "WITH SECURAL LINER".

In the Specification

Col. 1, in the heading, delete "WITH SECURAL LINER".

Col. 3, line 2, after "18" delete ",";
lines 5-6, delete "member" and insert -- members --;
line 10, after "includes" delete ",";
line 43, delete "side" and insert -- sidewalls --;

Col. 4, line 10, delete "member" and insert -- members --;
line 12, delete "member" and insert -- members --;
line 17, delete "member" and insert -- members --;
line 29, after "40" delete ",";
line 42, delete "member" and insert -- members --; and
line 49, delete "member" and insert -- members --.

Signed and Sealed this

Eleventh Day of March 1986

[SEAL]

Attest:

DONALD J. QUIGG

Attesting Officer

Commissioner of Patents and Trademarks